US012220348B2

(12) United States Patent
Rogers

(10) Patent No.: US 12,220,348 B2
(45) Date of Patent: Feb. 11, 2025

(54) THERMOTHERAPY PACK FOR THE GROIN

(71) Applicant: Freedom Products LLC, Orlando, FL (US)

(72) Inventor: Eric Thomas Rogers, Colorado Springs, CO (US)

(73) Assignee: Freedom Products, LLC, Orlando, FL (US)

( * ) Notice: Subject to any disclaimer, the term of this patent is extended or adjusted under 35 U.S.C. 154(b) by 733 days.

(21) Appl. No.: 17/203,124

(22) Filed: Mar. 16, 2021

(65) Prior Publication Data

US 2022/0296412 A1 Sep. 22, 2022

(51) Int. Cl.
*A61F 7/02* (2006.01)
*A61F 7/00* (2006.01)

(52) U.S. Cl.
CPC ........ *A61F 7/02* (2013.01); *A61F 2007/0048* (2013.01); *A61F 2007/0211* (2013.01); *A61F 2007/0219* (2013.01); *A61F 2007/0242* (2013.01); *A61F 2007/0246* (2013.01); *A61F 2007/0249* (2013.01); *A61F 2007/0282* (2013.01)

(58) Field of Classification Search
CPC .................. A61F 2007/0048; A61F 2007/005
See application file for complete search history.

(56) References Cited

U.S. PATENT DOCUMENTS

| 5,167,655 A | 12/1992 | McCoy |
| 9,393,151 B2 | 7/2016 | Gallen et al. |
| 2002/0193857 A1 * | 12/2002 | Lavine ...................... A61F 7/02 607/114 |
| 2012/0316626 A1 | 12/2012 | Dolivier et al. |

(Continued)

FOREIGN PATENT DOCUMENTS

| JP | 2006122640 | 5/2006 |
| KR | 1020140137524 | 12/2014 |
| WO | 2012170395 | 12/2012 |

OTHER PUBLICATIONS

Webpage https://www.amazon.co.uk/Vasectomy-Testicles-Injuries-Recovery-Treatment/dp/B07R1Z3DNR Date First Available Apr. 22, 2019 (Year: 2019).*

(Continued)

*Primary Examiner* — Kaitlyn E Smith
(74) *Attorney, Agent, or Firm* — Chad G. Clark; Martensen IP

(57) ABSTRACT

Disclosed is a therapy pack for applying thermotherapy to a user's groin for treatment of various conditions or injuries, and to aid in surgical recovery. The therapy pack has an insulated side and an uninsulated side, a two-lobed shape with a soft outer border, and contains a quantity of thermal storage material. The therapy pack also includes one or more window(s) without thermal storage material to reduce proximity of the material to genitalia. Embodiments include a three-window version and a single window version. Embodiments also include the use of one or more supplemental therapy pack(s) and a cover. Also disclosed is a method of using the therapy pack to apply thermotherapy to the male groin. Embodiments of the method include applying the therapy pack with the insulated side facing the user's skin, followed by applying the pack with the uninsulated side facing the skin.

5 Claims, 6 Drawing Sheets

(56) References Cited

U.S. PATENT DOCUMENTS

2013/0158635 A1     6/2013   Federico et al.
2013/0338742 A1    12/2013   Gallen et al.
2015/0173942 A1*   6/2015   Whitely .................... A61F 7/02
                                                                                         607/114

OTHER PUBLICATIONS https://www.amazon.co.uk/Vasectomy-Testicles-Injuries-Recovery-Treatment/product-reviews/B07R1Z3DNR/ref=cm_cr_getr_d_paging_btm_next_4?ie=UTF8&reviewerType=all_reviews&sortBy=recent&pageNumber=4 (Year: 2019).*

* cited by examiner

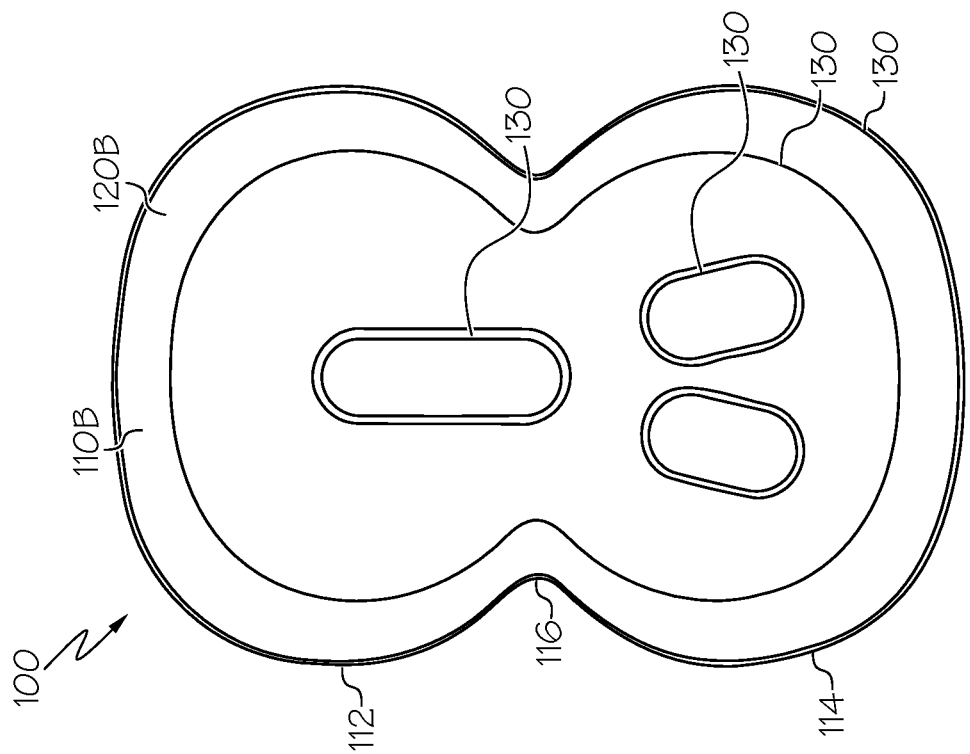
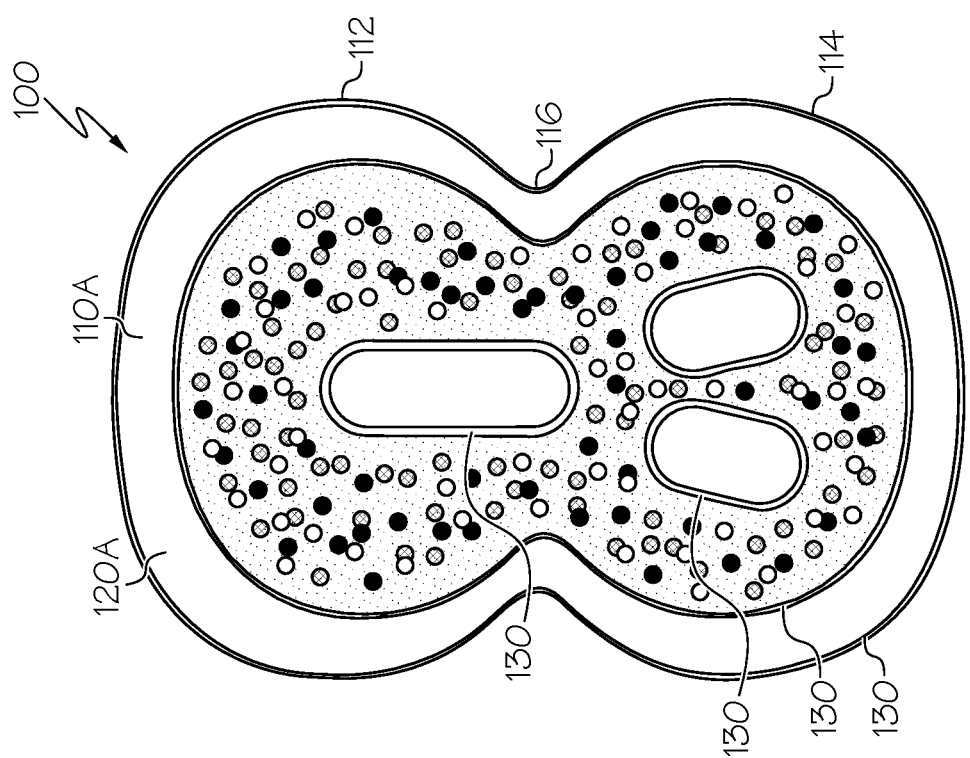

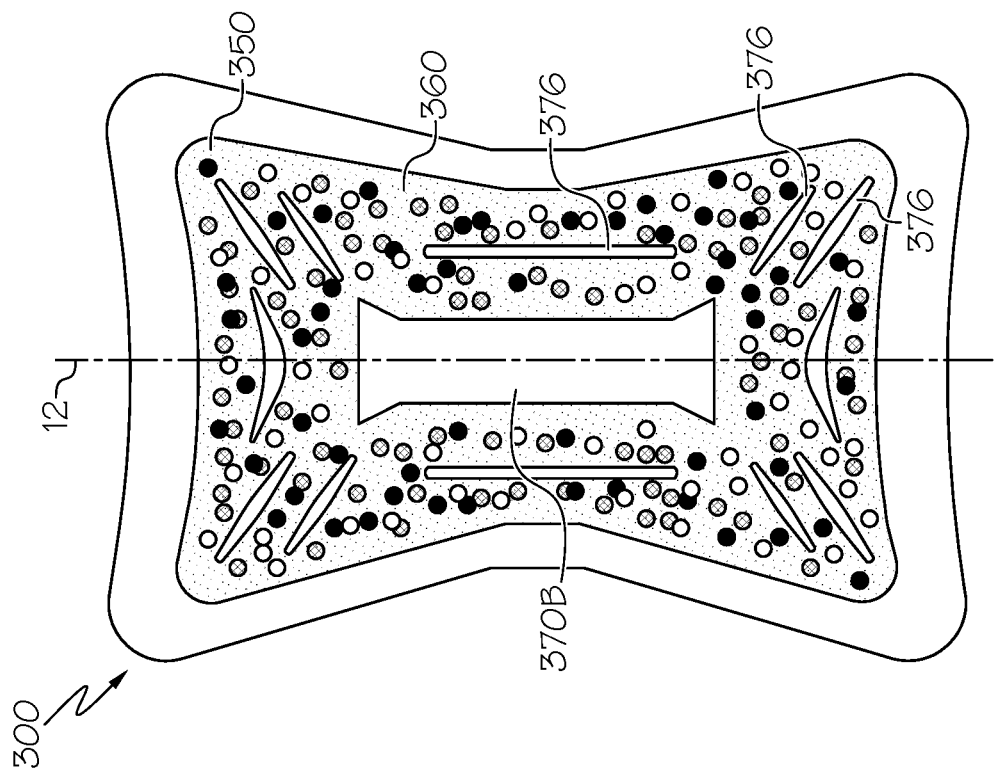
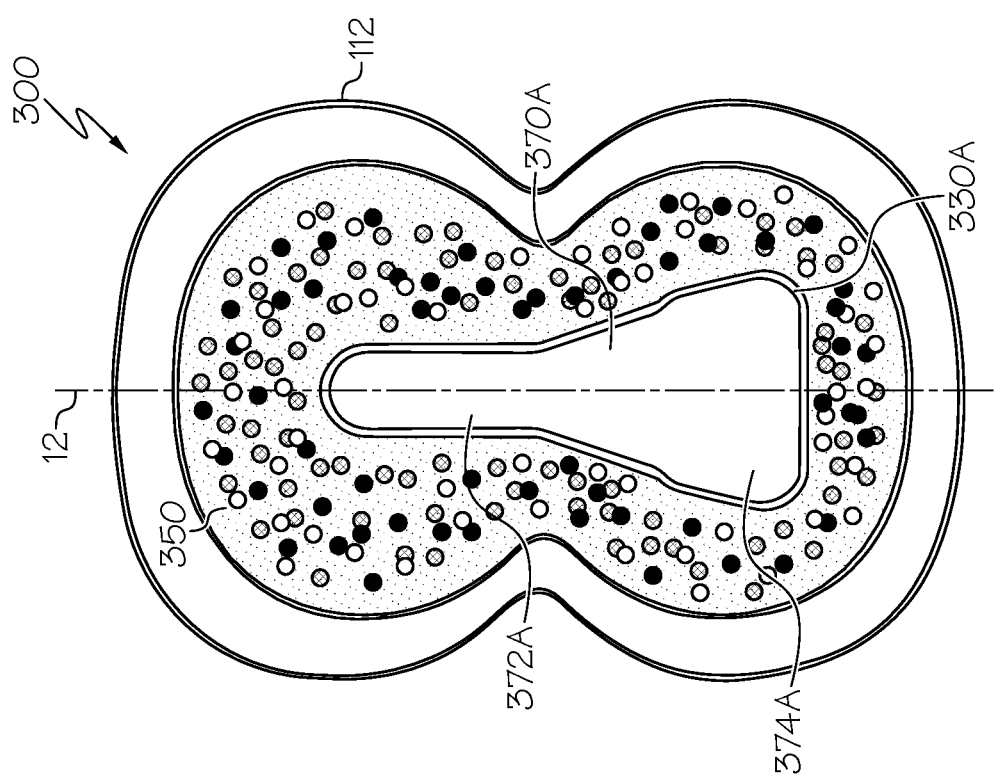

THERMOTHERAPY PACK FOR THE GROIN

CROSS-REFERENCE TO RELATED APPLICATIONS

None.

BACKGROUND

Field of the Invention

The present invention relates to devices for treating the human groin area with heat or cold therapy.

Relevant Background

For a number of reasons, the groin area can require heat or cold therapy. Such reasons include post-vasectomy recovery, post-delivery recovery, impact injuries, cycling and motorcycling soreness or injuries, illness, and hernia. Unfortunately, no existing products are designed specifically for use on the sensitive areas around the groin. As a result, existing art devices cut into, or otherwise interfere with, a user's legs, they can cause injury to genitalia through excessive heat or cold, are not suitable for both heat and cold therapy uses, and or lack the flexibility to be applied comfortably to the groin region, especially when frozen.

As is apparent from the above discussion, current devices have a number of shortcomings that expose device users to risk of injury, discomfort, or inconvenience. Therefore, it is apparent that a need exists for a therapy pack capable of providing either heat or cold therapy depending on the needs of the user, that is shaped for comfortable use in the groin area, and is designed to protect genitalia from excessive heat or cold.

The disclosed invention addresses the stated needs, in part, through a shape designed for comfortable wear on the groin, with a flexible outer border for improved comfort against sensitive skin. The therapy pack also includes specially formulated gel beads configured for hot and cold use, and further designed to provide heat or cold therapy within specified temperature limits, and to retain the flexibility required for use on the groin area. Finally, the therapy pack includes shaped regions without gel beads to protect sensitive genitalia from excessive temperatures.

A therapy pack with the disclosed features will greatly reduce the stated and obvious risks of using other, existing therapy packs for use on the groin. These and other deficiencies of the prior art are addressed by one or more embodiments of the disclosed invention. Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out hereafter.

BRIEF DESCRIPTION OF THE DRAWINGS

Features and objects of the present invention and the manner of attaining them will become more apparent, and the invention itself will be best understood, by reference to the following description of one or more embodiments taken in conjunction with the accompanying drawings and figures imbedded in the text below and attached following this description.

FIGS. 1A and 1B depict a front view and a back view of an embodiment of the disclosed therapy pack.

FIGS. 3A and 3B depict front views of embodiments of the disclosed therapy pack.

Figure 2:
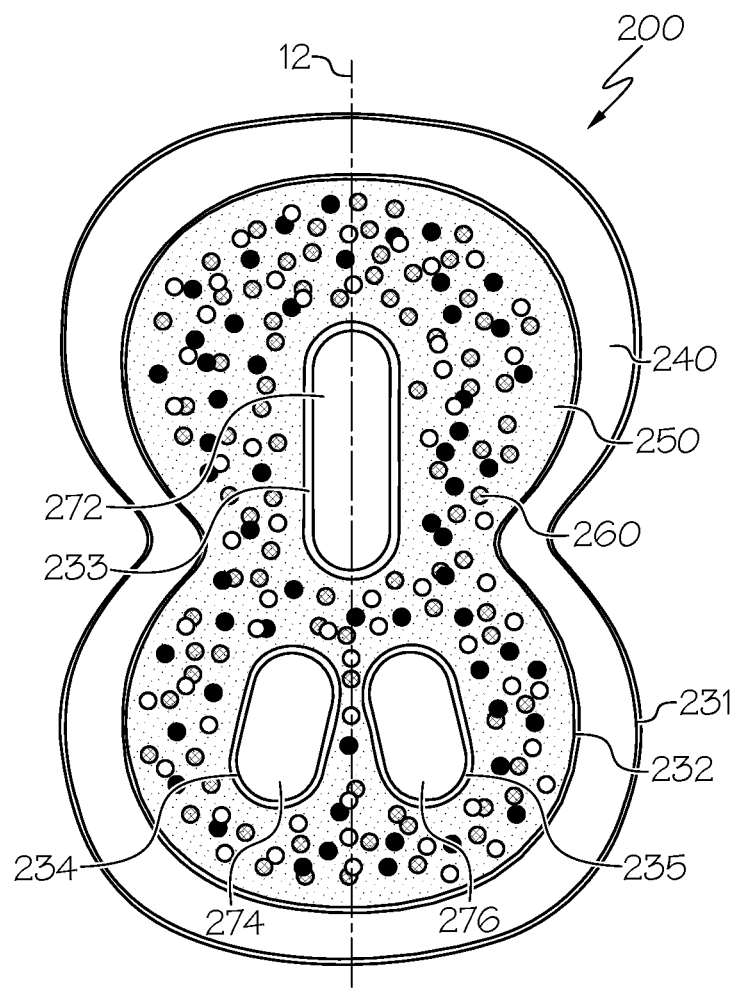
FIG. 2 depicts a front view of an embodiment of the disclosed therapy pack.

The Figures depict embodiments of the present invention for purposes of illustration only. One skilled in the art will readily recognize from the following discussion that alternative embodiments of the structures and methods illustrated herein may be employed without departing from the principles of the invention described herein.

DESCRIPTION

The disclosed thermotherapy pack provides a number of features that improve upon existing devices in the art. Unlike existing devices, the disclosed invention is specially designed for use on the groin area. Relevant features include an ergonomic shape to conform to the groin, genitalia, and legs when applied in a seated or prone position, the shape including two broad lobes connected by a narrow waist section, one or more window(s) designed to keep excessive temperatures from injuring genitalia, and a soft edge extending around the circumference of the therapy pack. The disclosed therapy pack also includes a plurality of gel beads formulated for storing and releasing heat or cold at a rate and level suitable for the treatment area. The gel beads are further designed to retain malleability and flexibility at extreme temperatures to promote comfortable application to the treatment area, and durability of the therapy pack over many uses. Potential uses include for post-medical procedure, e.g., vasectomy, sperm analysis, circumcision, post-childbirth, orchidectomy, vaginoplasty, labiaplasty; treatment for medical conditions, e.g., testicular torsion, hernia, kidney stones, sexually transmitted infections, strains, urinary tract infection, vaginitis; or for use after athletic or other physical activity, e.g., cycling, triathlon, motorcycling, endurance running.

The disclosed invention will now be described in detail with reference to several embodiments thereof as illustrated in the accompanying Figures. In the following description, numerous specific details are set forth in order to provide a thorough understanding of embodiments of the invention. It will be apparent, however, to one skilled in the art that embodiments may be practiced without some or all of these specific details. In other instances, well known process steps and/or structures have not been described in detail in order to not unnecessarily obscure the disclosed invention. The features and advantages of embodiments may be better understood with reference to the drawings and discussions that follow.

It should be apparent to those skilled in the art that the described embodiments of the disclosed invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the disclosed invention as defined herein and equivalents thereto. Hence, use of absolute and/or sequential terms, such as, for example, "always," "will," "will not," "shall," "shall not," "must," "must not," "first," "initially," "next," "subsequently," "before," "after," "lastly," and "finally," are not meant to limit the scope of the disclosed invention as the embodiments disclosed herein are merely exemplary.

It will be also understood that when an element is referred to as being "on," "attached" to, "connected" to, "coupled" with, "contacting", "mounted" etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of a device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

Thermotherapy Pack

The disclosed thermotherapy pack is designed for clinical use in cold therapy, and may also be used to apply heat therapy. The disclosed pack is also designed for use on the groin area of the human body to provide effective thermotherapy for areas around and near the genitalia. Some embodiments are designed to be suitable for male use, while other embodiments are designed to be suitable for female use.

FIGS. 1A and 1B depict a front view and a back view, respectively, of an embodiment of the disclosed therapy pack 100. The therapy pack has two sides, an uninsulated side 110A and an insulated side 110B. The uninsulated side 110A is comprised of a sheet 120A of preferably transparent or translucent polymer, e.g., nylon, polypropylene, polyvinyl chloride, polyurethane, polyethylene, ethylene-vinyl acetate, etc., but in some embodiments may be opaque. Latex is not used as a material. The sheet material is selected for a number of desired properties, including dimensional stability, flexibility over a broad range of temperatures, puncture-resistance, strength, water impermeability, and durability. Specifically, the material should retain its flexibility over temperatures from 20 Degrees Fahrenheit (° F.) to 110° F., and be conformable to the body. Durability includes the ability to withstand a large number of folding cycles over the temperature range without cracking or leaking.

The insulated side 110B is made of a sheet of material having a cloth-like surface 120B on one side, wherein the cloth-like surface is oriented toward the outside of the pack. The material comprising the insulated side may be the same as the material 120A used for the uninsulated side, or may be another material suited for providing the required insulating properties. The cloth-like surface may be adhered to the sheet of material, or may be one surface of the material treated to create the cloth-like surface. The cloth-like surface is soft and flexible, and provides a degree of insulation between a user's skin and the thermal storage material by trapping air among its fibers. The therapy pack may also be used with a cloth-like cover (not shown). The cover is soft, flexible, and provides a degree of insulation to the therapy pack when it is placed inside the cover. Therefore, the therapy pack allows up to four different temperature applications ranging from least to most gentle: uninsulated side direct, insulated side direct, uninsulated through the cover, and insulated through the cover.

The therapy pack 100 is shaped with an upper lobe 112 and a lower lobe 114 connected by a waist 116, which together give the pack a peanut-shaped footprint. The therapy pack is comprised of a number of zones created by a plurality of seals 130 for joining components and or containing materials. The seals 130 are robust, flexible, leak-proof bonds between the uninsulated 120A and insulated 120B layer materials, and are created by, for example, fusing the layers of the therapy pack together through plastic welding techniques, such as heat welding, ultrasonic welding, or friction welding, or may be created by adhesive bonds. Embodiments of the therapy pack may include a plurality of different sizes to meet the needs of different users. A Large-sized therapy pack is 346 mm long and 226 mm wide (at the widest portion of the lobes 112, 114), and 156 mm wide across the waist. The waist is indented about 35 mm from the widest portion of the upper and lower lobes, which provides additional room to accommodate variations in anatomy size and or shape. Other sizes available may include Small, Medium, and Extra Large, which are sized proportionally larger or smaller than the Large size described herein.

With reference to FIG. 2, an embodiment of the uninsulated side of the therapy pack 200 is depicted. The pack includes an outer lip or border 240, a cavity or compartment 250 for containing thermal storage material 260, and one or more protection windows 272, 274, 276 (three are shown). The outer border 240 is a flat area that extends around the circumference of the pack and is comprised of the two sheets of material (FIGS. 1A-1B, items 120A, 120B). The outer border 240 is delineated by two seals, a first seal 231 along the outer edge of the pack and a second seal 232 along the outer edge of the compartment 250. The outer border 240 improves user comfort by creating a soft edge for the pack where it interfaces with the user's legs, and by providing a buffer between the edge of the pack and the thermal storage material in the compartment. The outer border is preferably 10 millimeters (mm) in width, but in some embodiments may be 5 mm, 15 mm, or 20 mm in width.

The window(s) 272, 274, 276 are areas that are comprised of the two sheets of material (FIGS. 1A-1B, items 120A, 120B) that have thermal storage material 260 excluded by use of seals 233, 234, 235. A standard window configuration suitable for use on a male groin includes an elongated window 272 for the penis and two angled windows for the testicles 274, 276. The windows are oriented along the centerline of the therapy pack, shown as a dotted line 12. The elongated window 272 is centered lengthwise on the centerline 12, and extends roughly from the waist into the upper lobe of the pack. On the Large therapy pack, the elongated window measures 110 mm long and 40 mm wide. The angled windows 274, 276, are arranged on either side of the centerline 12, and are angled 15 Degrees (°) toward the centerline. The angled windows are 70 mm long and 40 mm wide on the Large therapy pack. Use of windows removes thermal material from direct proximity to the genitals, but allows heat or cold to be administered to adjacent areas that need therapy. The area between the angled windows contains thermal storage material, and is 10 mm wide at its narrowest point. The area between the angled windows and the elongated window contains thermal storage material and is 30 mm wide at its narrowest point. Both the size and volume of thermal storage material in these interstitial areas are important for effective therapy of male genitals.

With reference to FIGS. 3A and 3B, embodiments of the disclosed therapy pack 300 may feature alternate window configurations. FIG. 3A depicts a therapy pack for use on a male groin that includes a single window 370A for protecting male genitalia. The window 370A is centered on the centerline 12 of the pack, and features an elongated area 372A for protecting the penis, as well as a wider section 374A for protecting the testicles. The single window 370A may provide enhanced comfort for some users by allowing a larger protected area for the genitalia, without intervening areas with thermal storage material. FIG. 3B depicts a therapy pack for use on a female groin featuring a single window 370B shaped for protecting the female genitalia. The window 370B is centered on the centerline 12 of the pack, which has an hourglass shape to better fit female anatomy. The pack designed for female use also includes a plurality of spacers 376, which are sealed areas which exclude thermal storage material 360, and which serve to restrict and direct the movement of material within the storage compartment 350. The spacers 376 maintain an even distribution of the material 360 so that it does not collect in any one area, which potentially could expose sensitive areas to excess heat or cold. The spacers 376 may be arranged in a number of ways as long as they promote the correct, substantially uniform distribution of material 360.

Figure 4:
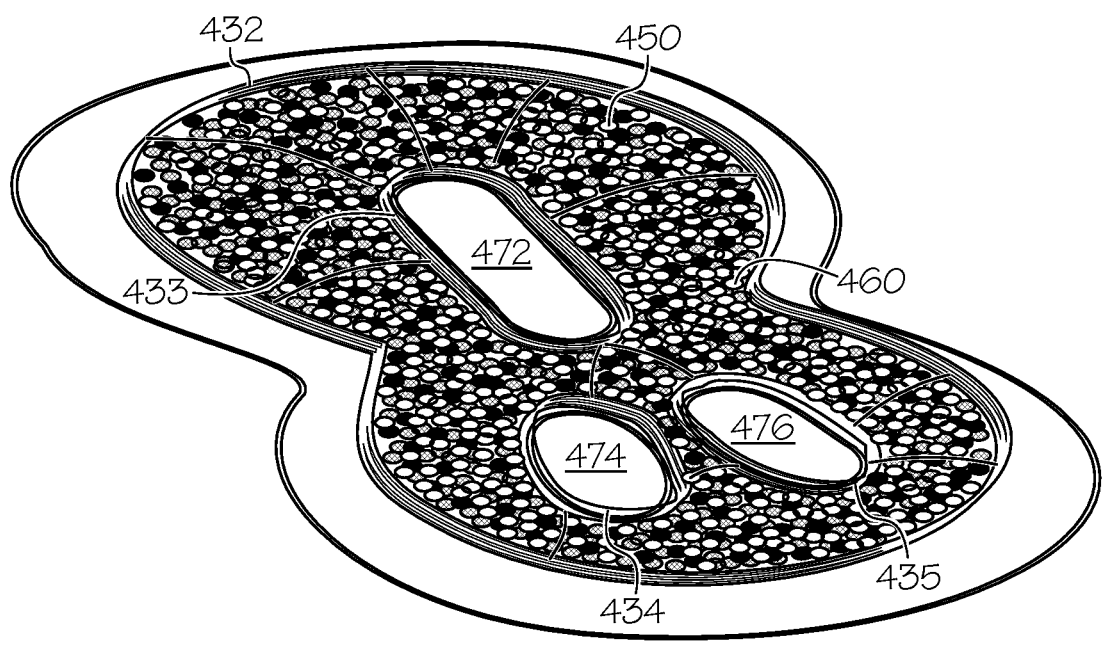
FIG. 4 depicts a quadrant view of the front of an embodiment of the disclosed therapy pack.

With reference to FIG. 4, which is a quadrant view of the uninsulated side of the pack, the compartment 450 is a sealed container for holding the thermal storage material 460, and in the Large size is 200 mm wide at its widest point, 130 mm wide at the waist, and 320 mm long. The cavity 450 is delineated by the second seal 432, and is bounded internally by one or more seals 433, 434, 435, that create the protection windows 472, 474, 476 (three seals and three windows are shown). In some embodiments, the thermal storage material 460 is a plurality of beads made of glycerin gel. The gel contains at least 30% glycerin, but some embodiments may have between 30% glycerin and 50% glycerin. The glycerin percentages used in the therapy pack are designed to provide a maximum duration during which the pack will remain cold enough for effective treatment, but does not freeze solid. For the Large sized therapy pack, the volume of thermal beads 460 within the cavity 450 is about 470 grams (g), however some embodiments may include from about 350 g up to about 550 g. The disclosed thermal beads are soft to improve user comfort, and are designed to have energy storage and release properties for optimal treatment of the sensitive areas of the groin. Further, the disclosed thermal beads remain individually malleable and collectively flexible across the required temperature range. In some embodiments, other thermal storage material may be used, for example, silica gels, hydroxyethyl cellulose gels, polymer gels, phase-change gels, clay, or beads made of such materials. The therapy pack is designed to provide 30 minutes of heat or cold therapy.

Figure 5:
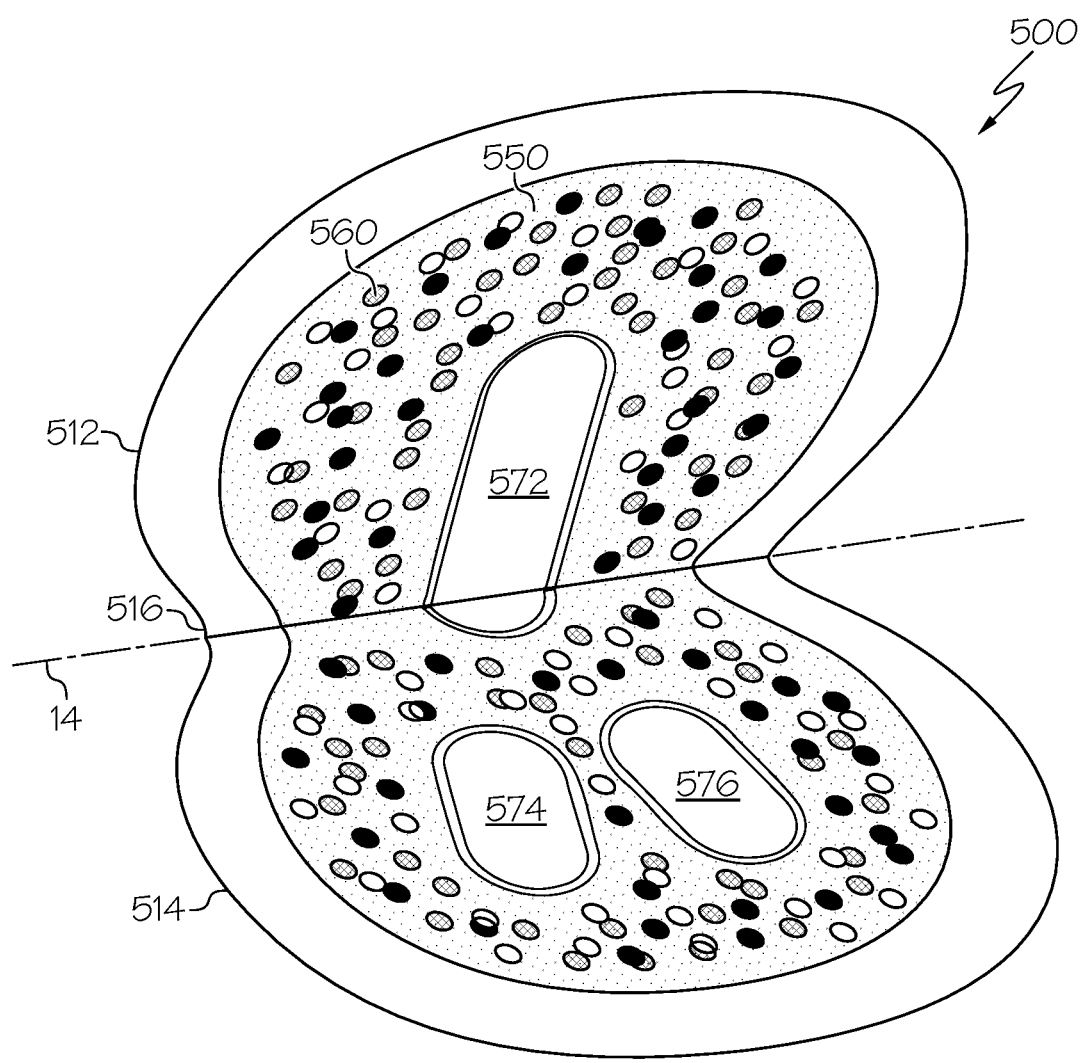
FIG. 5 depicts a quadrant view of the front of an embodiment of the disclosed therapy pack as folded for use.

With reference to FIG. 5, a view of the standard three-window therapy pack 500 is depicted as it may appear in use. The user first places the therapy pack in a freezer for cold therapy, or places the pack in a microwave oven for heat therapy. Once the desired temperature is achieved, the pack is removed from the freezer or microwave and prepared for application. The pack is shown folded along a line across the waist portion of the pack as depicted by the dotted line 14. A user places the lower lobe 514 of the pack under the legs and below the scrotum, and positions the testicles to rest on top of the angled windows 574, 576. The user then preferably arranges the penis to point toward the user's navel and aligns the penis with the elongated window 572 as the top lobe 512 is placed against the lower abdomen and held in pace. For comfort and to reduce the risk of heat or cold injury, the user may begin a therapy session by placing the therapy pack on the groin with the insulated side facing the skin, or the therapy pack may first be placed inside the cover before application. As the pack equilibrates to the outside environment, the user may turn it over so that the uninsulated side faces the skin. Cold therapy duration and temperature are at the user's discretion or a physician's prescription. Heat therapy is only contemplated under a physician's prescription.

Figure 6A:
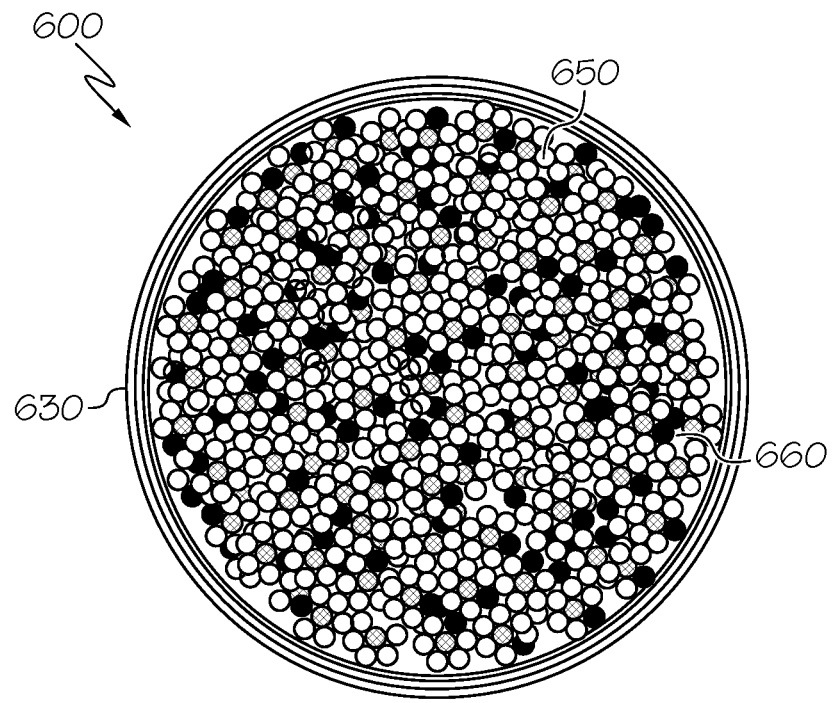
FIG. 6A depicts a top view.
Figure 6B:
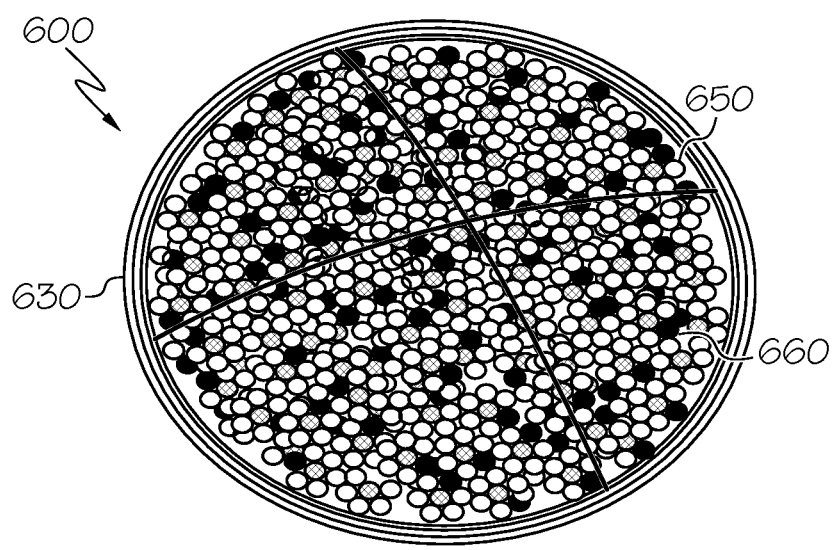
FIG. 6B depicts a quadrant view of an auxiliary therapy pack for use with the disclosed therapy pack.

With reference to FIGS. 6A and 6B, different views of an embodiment of a supplemental therapy pack 600 are depicted. FIG. 6A depicts a top view of the supplemental therapy pack 600, which is constructed of two sheets of the same material as the uninsulated side of the therapy pack (see FIG. 1A, item 120A). In alternate embodiments of the supplemental pack 600, one or both sides have insulating material as is used for the insulated side of the therapy pack (see FIG. 1B, item 120B). The two sheets of material are sealed together at an outer edge seal 630, creating a cavity or compartment 650 that holds thermal storage material 660. The thermal storage material is, e.g., glycerin gel beads, wherein the gel contains about 25% glycerin. FIG. 6B depicts a top quadrant view of the pack showing that the cavity with thermal storage material has a thickness. The supplemental pack 600 may be a circle of 85 mm in diameter with a thickness of about 15 mm. While the supplemental pack 600 is depicted as circular in shape, other suitable shapes not having sharp corners are possible and contemplated. The supplemental pack 600 is used, for example, to add intensity to therapy in hard-to-reach areas below the male scrotum, or below the sit bones, or may extend the therapy session by adding supplemental packs several minutes after the main therapy pack is applied.

While this invention has been described in terms of several embodiments, there are alterations, modifications, permutations, and substitute equivalents, which fall within the scope of this invention. Although subsection titles have been provided to aid in the description of the invention, these titles are merely illustrative and are not intended to limit the scope of the present invention. In addition, where claim limitations have been identified, for example, by a numeral or letter, they are not intended to imply any specific sequence. It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

This has been a description of the disclosed invention along with a preferred method of practicing the invention, however, the invention should be defined by the appended claims.

What is claimed is:

1. A method for applying thermotherapy to the male groin, the method comprising:
providing a therapy pack wherein the therapy pack comprises an insulated side having insulation designed to impede the flow of thermal energy through the insulation; an uninsulated side; a shape comprising an upper lobe and a lower lobe that are joined at a waist, wherein the upper lobe and lower lobe are symmetrical when bisected along a center line, and wherein the shape is symmetrical when bisected across the waist; a thermal storage compartment for holding material for thermal energy storage and release; a border located around the thermal storage compartment, wherein the border includes an inner seal and an outer seal, and wherein the border is configured to interface with a pack user's legs and provide a buffer zone between the pack user's legs and the thermal storage compartment; and one or more windows designed to exclude the material, the one or more windows arranged along the center line in location(s) corresponding to the user's genitalia;
storing thermal energy in the therapy pack by on of: heating the therapy pack in a microwave oven, or cooling the therapy pack in a freezer;
applying the therapy pack to the groin, the application comprising:
placing the lower lobe partially under a pack user's legs and resting the user's testicles on the one or more windows, folding the therapy pack along the waist and aligning the user's penis with the one or more windows, placing the upper lobe on the user's abdomen, placing one or more supplemental therapy pack(s) between the user and the lower lobe; and
removing the therapy pack.

2. The method of claim 1, further comprising the step of placing the therapy pack in the cover prior to the application step.

3. The method of claim 2, further comprising removing the therapy pack from the cover and repeating the application step and the removal step.

4. The method of claim 1, the application step comprising:
orienting the therapy pack with the insulated side facing the user's groin, removing the therapy pack and orienting the pack with the uninsulated side facing the user's groin, placing the lower lobe partially under the pack user's legs and resting the user's testicles on the one or more windows, folding the therapy pack along the waist and aligning the user's penis with the one or more windows, and placing the upper lobe on the user's abdomen.

5. The method of claim 1, wherein the waist is 35 mm narrower than the widest portions of the upper lobe and the lower lobe.

* * * * *